(12) United States Patent
Bollu et al.

(10) Patent No.: US 10,844,048 B2
(45) Date of Patent: Nov. 24, 2020

(54) PROCESS AND CRYSTALLINE FORMS OF LUMACAFTOR

(71) Applicant: LAURUS LABS LIMITED, Hyderabad (IN)

(72) Inventors: Ravindra Babu Bollu, Hyderabad (IN); Prasanta Kumar Dalasingh, Hyderabad (IN); Sushmita Dwarampudi, Hyderabad (IN); Chandrahasa Reddy Annem, Hyderabad (IN); Uma Maheswer Rao Vasireddi, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 0 days.

(21) Appl. No.: 16/476,486

(22) PCT Filed: Jan. 6, 2018

(86) PCT No.: PCT/IB2018/050095
§ 371 (c)(1),
(2) Date: Jul. 8, 2019

(87) PCT Pub. No.: WO2018/127846
PCT Pub. Date: Jul. 12, 2018

(65) Prior Publication Data
US 2019/0375734 A1    Dec. 12, 2019

(30) Foreign Application Priority Data
Jan. 9, 2017 (IN) .............................. 201741000812

(51) Int. Cl.
*C07D 405/12* (2006.01)

(52) U.S. Cl.
CPC ........ *C07D 405/12* (2013.01); *C07B 2200/13* (2013.01)

(58) Field of Classification Search
CPC .. C07D 405/12; C07B 2200/13; A61K 45/06; A61K 31/443
USPC ....................................................... 546/284
See application file for complete search history.

(56) References Cited

FOREIGN PATENT DOCUMENTS

| WO | WO-2007/056341 A1 | 5/2007 |
|----|-------------------|--------|
| WO | WO/2007-056341 A1 | 5/2007 |
| WO | WO/2009-073757 A1 | 6/2009 |
| WO | WO/2011-127290 A2 | 10/2011 |

OTHER PUBLICATIONS

International Search Report for PCT/IB2018/050095 dated Mar. 13, 2018.

*Primary Examiner* — Taylor V Oh
(74) *Attorney, Agent, or Firm* — Blank Rome LLP

(57) ABSTRACT

The present invention generally relates to crystalline forms of Lumacaftor, processes for its preparation and pharmaceutical compositions thereof. The present invention also relates to an improved process for preparation of Lumacaftor.

22 Claims, 9 Drawing Sheets

PROCESS AND CRYSTALLINE FORMS OF LUMACAFTOR

CROSS-REFERENCE TO RELATED APPLICATIONS

This is a national phase application of and claims the benefit of International Application PCT/IB2018/050095, filed on 6 Jan. 2018, which is based on and claims the benefit of the filing date and disclosure of Indian Provisional Application No. 201741000812, filed on 9 Jan. 2017, entitled "Process and crystalline forms of lumacaftor", the contents of which are incorporated by reference herein.

FIELD OF THE INVENTION

The present invention generally relates to crystalline forms of Lumacaftor, processes for its preparation and pharmaceutical compositions thereof. The present invention also relates to an improved process for the preparation of Lumacaftor.

BACKGROUND OF THE INVENTION

3-{6-{[1-(2,2-Difluoro-1,3-benzodioxol-5-yl)cyclopropanecarbonyl]amino}-3-methyl pyridine-2-yl}benzoic acid, commonly known as Lumacaftor having the compound of Formula I, is a modulator of CFTR activity and thus useful in treating CFTR-mediated diseases such as cystic fibrosis (CF).

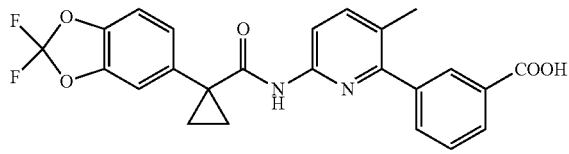

Formula I

Cystic Fibrosis (CF) is a fatal autosomal recessive disease associated with defective hydration of lung airways due to the loss of function of the CF transmembrane conductance regulator (CFTR) channel at epithelial cell surfaces.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population. Lumacaftor has been demonstrated to restore the function of the cystic fibrosis transmembrane conductance regulator (CFTR) protein.

Lumacaftor is available in a single pill with Ivacaftor combination, lumacaftor/ivacaftor having the brand name Orkambi®, is used to treat people with cystic fibrosis who have the F508del mutation in the cystic fibrosis transmembrane conductance regulator (CFTR). Lumacaftor was developed by Vertex Pharmaceuticals and the Lumacaftor/Ivacaftor combination was approved by the FDA in 2015.

PCT publication No. 2007/056341 ("the '341 publication") discloses modulators of ATP-Binding Cassette ("ABC") transporters including Cystic Fibrosis Transmembrane conductance Regulator ("CFTR") such as lumacaftor. The '341 publication discloses a process for preparation of lumacaftor by reaction of Formula II (chloro intermediate) with Formula III by microwave irradiation at a temperature of about 150° C. to obtain lumacaftor, which is purified by reverse-phase preparative liquid chromatography. The process disclosed in the '341 publication is schematically represented as follows:

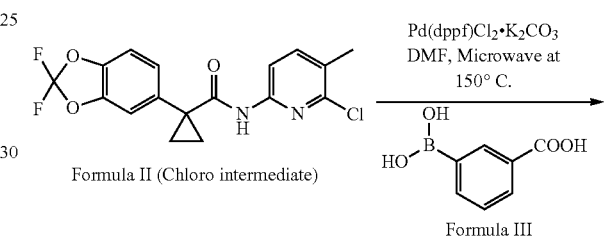

The synthesis of lumacaftor as disclosed in the '341 publication has certain drawbacks as it involves:
a) reaction of Formula II (chloro intermediate) with Formula III involves microwave irradiation at 150° C. The use of special techniques such as reaction by microwave irradiation is not viable for commercial scale operations as this technique involves specialized expensive equipment's, and
b) involves tedious reverse-phase preparative liquid chromatography purifications, which contributes significant impact on the final yield and purity, makes the process not viable for large scale manufacturing.

PCT Publication No. 2009/073757 ("the '757 publication") disclosed crystalline Form I of lumacaftor. The '757 publication also discloses alternative process for preparation of lumacaftor. The '757 publication exemplified process involves lengthy process like using ester intermediate as starting material and followed by hydrolysis of the ester group at final step to obtain lumacaftor. The process disclosed in the '757 publication is schematically represented as follows:

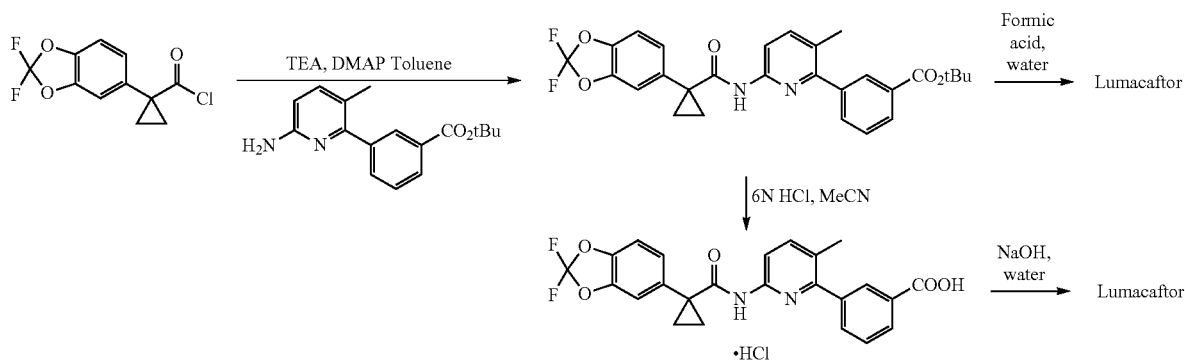

PCT Publication No. 2011/127290 ("the '290 publication") disclosed crystalline Form A of lumacaftor hydrochloride salt and further disclosed various isostructural solvates of lumacaftor such as methanol solvate, ethanol solvate, acetone solvate, 2-propanol solvate, acetonitrile solvate, tetrahydrofuran solvate, methyl acetate solvate, 2-butanone solvate, ethyl formate solvate and 2-methyl tetrahydrofuran solvate and process for their preparation, wherein the process for preparing isostructural solvates involves the slurring of solvate reaction mixture for 48 hours.

Indian Publication No.(s) 201641000118, 201621004780 & 5209/CHE/2015 disclosed process for preparation of amorphous form of lumacaftor.

CN Publication No. 106432209 disclosed preparation of crystalline form A of lumacaftor from methyl isobutyl ketone and a mixture of methyl isobutyl ketone and acetone.

PCT Publication No. 2017/017696 ("the '696 publication") disclosed preparation of lumacaftor. The process disclosed in the '696 publication is schematically represented as follows:

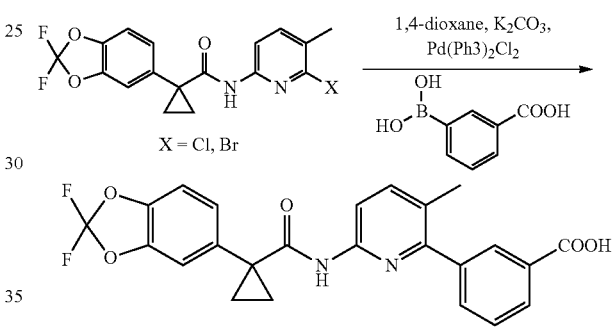

PCT Publication No. 2017/056031 ("the '031 publication") disclosed preparation of lumacaftor. The process disclosed in the '031 publication is schematically represented as follows:

PCT Publication No. 2017/175161 ("the '161 publication") disclosed preparation of lumacaftor. The '161 publication also disclosed hydrobromide salt of lumacaftor, crystalline form SV1-SV4 of lumacaftor and its process for preparation thereof. The process disclosed in the '161 publication is schematically represented as follows:

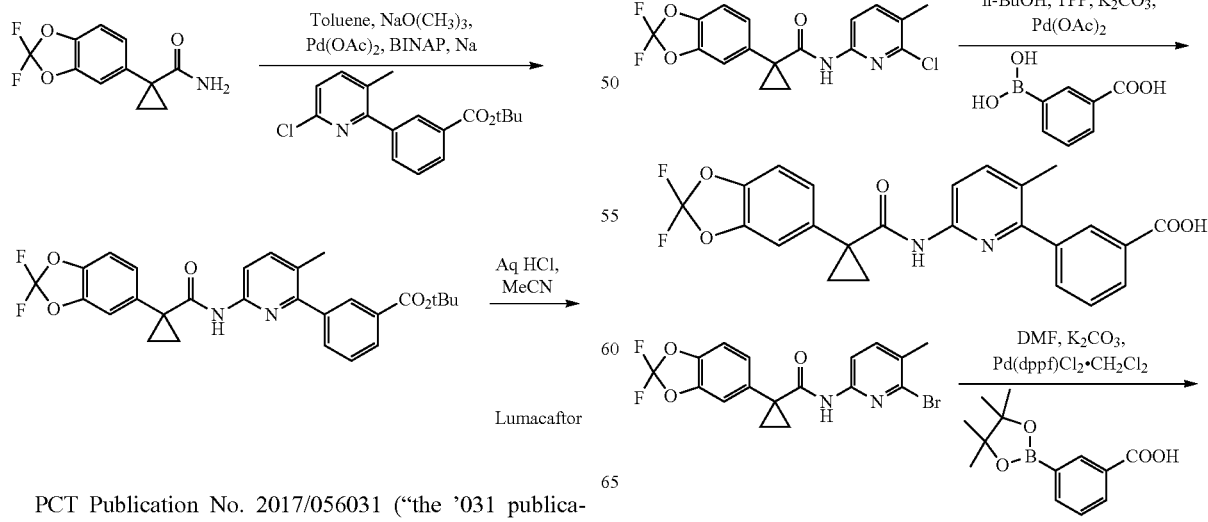

-continued

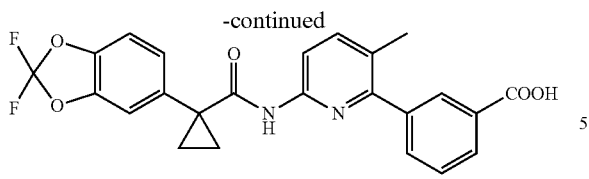

PCT Publication No. 2017/118915 ("the '915 publication") disclosed amorphous form of lumacaftor and its process for preparation thereof. Further, the '915 publication disclosed crystalline complex of lumacaftor and ivacaftor and its process for preparation thereof.

PCT Publication No. 2017/137900 ("the '900 publication") disclosed amorphous form of lumacaftor and its process for preparation thereof. Further, the '900 publication disclosed crystalline form A of lumacaftor hydrobromide salt.

PCT Publication No. 2017/025045 ("the '045 publication") disclosed crystalline form A of lumacaftor and its process for preparation thereof.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms and solvates, and to determine the stability, dissolution and flow properties of each polymorphic form. Polymorphic forms and solvates of a compound can be distinguished in a laboratory by X-ray diffraction spectroscopy and by other methods such as, infrared spectrometry. Additionally, polymorphic forms and solvates of the same drug substance or active pharmaceutical ingredient, can be administered by itself or formulated as a drug product (also known as the final or finished dosage form), and are well known in the pharmaceutical art to affect, for example, the solubility, stability, flowability, tractability and compressibility of drug substances and the safety and efficacy of drug products.

The discovery of new crystalline polymorphic forms and solvates of a pharmaceutically useful compound, like lumacaftor, may provide a new opportunity to improve the performance characteristics of a pharmaceutical product. It also adds to the material that a formulation scientist has available for designing, for example, a pharmaceutical dosage form of a drug with a targeted release profile or other desired characteristic. New crystalline polymorphic forms of the lumacaftor have now been discovered and have been designated as Form LA1, Form LA2 and Form LA3.

Based on the process drawbacks mentioned in the '341 and '757 publications, there is a vital need to develop a process for the preparation of lumacaftor, which is readily amenable to large scale production.

Hence, present inventors focused research to simplify the process for the preparation of lumacaftor, which avoids mainly microwave irradiation thereby avoiding the formation of impurities and making the process more suitable for commercial applications with higher purity and obviate the problems associated with the reported processes.

SUMMARY OF THE INVENTION

The present invention provides novel crystalline forms of lumacaftor, process for their preparation and pharmaceutical compositions comprising one or more of the novel crystalline forms of lumacaftor. The present invention also relates to an improved process for preparation of lumacaftor.

In accordance with one embodiment, the present invention provides novel crystalline forms of lumacaftor.

In accordance with another embodiment, the present invention provides novel crystalline forms of lumacaftor, herein designated as lumacaftor Form-LA1, lumacaftor Form-LA2 and lumacaftor Form-LA3.

In accordance with another embodiment, the lumacaftor Form-LA1 of the present invention is an anhydrous crystalline from.

In accordance with another embodiment, the present invention provides crystalline lumacaftor Form-LA1 characterized by a X-ray powder diffraction in accordance with FIG. 1.

In accordance with another embodiment, the present invention provides crystalline lumacaftor Form-LA1 characterized by a differential scanning calorimetry (DSC) thermogram substantially in accordance with FIG. 2.

In accordance with another embodiment, the present invention provides crystalline lumacaftor Form-LA1 characterized by a thermo gravimetric analysis (TGA) curve substantially in accordance with FIG. 3.

In accordance with another embodiment, the present invention provides crystalline lumacaftor Form-LA1, characterized by a powder X-Ray diffraction (PXRD) pattern substantially in accordance with FIG. 1, a differential scanning calorimetry (DSC) substantially in accordance with FIG. 2 and a thermo gravimetric analysis (TGA) substantially in accordance with FIG. 3.

In accordance with another embodiment, the present invention provides a process for the preparation of lumacaftor Form-LA1, comprising:
 a) dissolving lumacaftor in water and a suitable base at a suitable temperature,
 b) optionally, cooling the solution to less than 25° C., and
 c) isolating the lumacaftor Form-LA1.

In accordance with another embodiment, the present invention provides a process for the preparation of lumacaftor Form-LA1, comprising:
 a) dissolving lumacaftor in water and a suitable base at a suitable temperature,
 b) optionally, cooling the solution to less than 25° C., and
 c) isolating the lumacaftor Form-LA1; wherein the suitable base is selected from the group comprising ammonium bases, alkali metal hydroxides, alkali metal alkoxides, alkali metal carbonates, alkali metal bicarbonates or organic bases and mixture thereof.

In accordance with another embodiment, the present invention provides a process for the preparation of lumacaftor Form-LA1, comprising:
 a) dissolving lumacaftor in water and a suitable base at a temperature of about 35° C. to about reflux temperature,
 b) optionally, cooling the solution to less than 25° C., and
 c) isolating the lumacaftor Form-LA1; wherein the suitable base is selected from the group comprising ammonium bases, alkali metal hydroxides, alkali metal alkoxides, alkali metal carbonates, alkali metal bicarbonates or organic bases and mixture thereof.

In accordance with another embodiment, the present invention provides a process for the preparation of lumacaftor Form-LA1, comprising:
a) dissolving lumacaftor in water and ammonium hydroxide at a temperature of about 35° C. to reflux temperature,
b) optionally, cooling the solution to less than 25° C., and
c) isolating the lumacaftor Form-LA1.

In accordance with another embodiment, the present invention provides a process for the preparation of lumacaftor Form-LA1, comprising:
a) suspending lumacaftor in water,
b) adding ammonium hydroxide to the step a) suspension or vice-versa,
c) heating the step b) reaction mixture to about 35° C. to reflux temperature,
d) cooling the step c) reaction mixture to less than 25° C., and
e) isolating the lumacaftor Form-LA1.

In accordance with another embodiment, the lumacaftor Form-LA2 of the present invention is an ammonia solvate.

In accordance with another embodiment, the present invention provides crystalline lumacaftor Form-LA2 characterized by a X-ray powder diffraction in accordance with FIG. 4.

In accordance with another embodiment, the present invention provides crystalline lumacaftor Form-LA2 characterized by a differential scanning calorimetry (DSC) thermogram substantially in accordance with FIG. 5.

In accordance with another embodiment, the present invention provides crystalline lumacaftor Form-LA2 characterized by a thermo gravimetric analysis (TGA) curve substantially in accordance with FIG. 6.

In accordance with another embodiment, the present invention provides crystalline lumacaftor Form-LA2, characterized by a powder X-Ray diffraction (PXRD) pattern substantially in accordance with FIG. 4, a differential scanning calorimetry (DSC) substantially in accordance with FIG. 5 and a thermo gravimetric analysis (TGA) substantially in accordance with FIG. 6.

In accordance with another embodiment, the present invention provides a process for the preparation of lumacaftor Form-LA2, comprising: exposing lumacaftor Form-LA1 under ammonia atmosphere.

In accordance with another embodiment, the lumacaftor Form-LA3 of the present invention is an anhydrous crystalline from.

In accordance with another embodiment, the present invention provides crystalline lumacaftor Form-LA3 characterized by a X-ray powder diffraction in accordance with FIG. 7.

In accordance with another embodiment, the present invention provides crystalline lumacaftor Form-LA3 characterized by a differential scanning calorimetry (DSC) thermogram substantially in accordance with FIG. 8.

In accordance with another embodiment, the present invention provides crystalline lumacaftor Form-LA3 characterized by a thermo gravimetric analysis (TGA) curve substantially in accordance with FIG. 9.

In accordance with another embodiment, the present invention provides crystalline lumacaftor Form-LA3, characterized by a powder X-Ray diffraction (PXRD) pattern substantially in accordance with FIG. 7, a differential scanning calorimetry (DSC) substantially in accordance with FIG. 8 and a thermo gravimetric analysis (TGA) substantially in accordance with FIG. 9.

In accordance with another embodiment, the present invention provides a process for the preparation of lumacaftor Form-LA3, comprising: heating lumacaftor Form-LA1 at about 100° C. to about 140° C. for about 3 to 12 hours.

In accordance with another embodiment, the present invention provides an improved process for the preparation of lumacaftor with high product yield and quality, wherein the improvements comprise use of conventional synthesis, which avoids cumbersome microwave irradiation, thereby avoiding the formation of impurities.

In accordance with another embodiment, the present invention provides an improved process for the preparation of lumacaftor of Formula I,

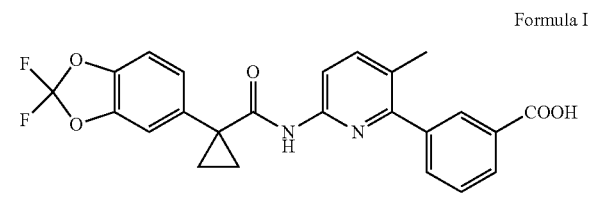 [SMILES: Cc1ccc(NC(=O)C2(c3ccc4c(c3)OC(F)(F)O4)CC2)nc1-c1cccc(C(=O)O)c1]

Formula I comprising: reacting a compound of Formula II; wherein 'X' represent a suitable leaving group, with a compound of Formula III in presence of a palladium catalyst and base in a suitable solvent to obtain lumacaftor.

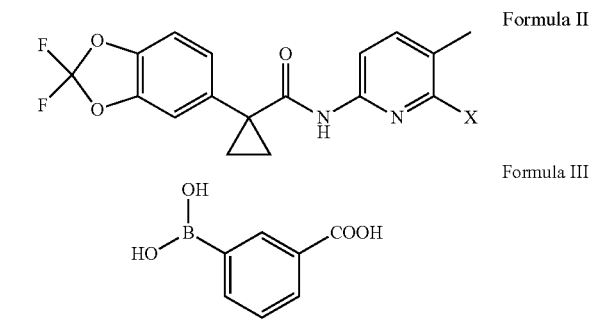

Formula II

Formula III

In accordance with another embodiment, the present invention provides a process for the preparation of lumacaftor Form-LA1, comprising:
a) reacting a compound of Formula II; wherein 'X' represent a suitable leaving group, with a compound of Formula III in presence of a palladium catalyst and base in a suitable solvent to obtain lumacaftor,
b) dissolving lumacaftor from step a) in water and a suitable base at a suitable temperature,
c) optionally, cooling the solution to less than 25° C., and
d) isolating the lumacaftor Form-LA1.

In accordance with another embodiment, the present invention provides the use of novel crystalline forms of lumacaftor Form-LA1, Form-LA2 or Form-LA3 as an intermediate to prepare other polymorphic forms of lumacaftor.

In accordance with another embodiment, the present invention provides a process for the preparation of lumacaftor Form I, comprising:
a) suspending lumacaftor Form-LA1 in a suitable solvent; and
b) isolating the lumacaftor Form I.

In accordance with another embodiment, the present invention provides a pharmaceutical composition comprising lumacaftor or a combination of lumacaftor and Ivacaftor, prepared by the process of the present invention and at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Unless otherwise specified in this specification, "solvate" herein used in this specification, refers to a crystals form that incorporates a solvent in the crystal structure. The solvent in a solvate may be present in either a stoichiometric or in a non-stoichiometric amount.

The present invention provides novel crystalline forms of lumacaftor, process for their preparation and pharmaceutical compositions comprising one or more of the novel crystalline forms of lumacaftor. The present invention also relates to an improved process for preparation of lumacaftor.

As used herein, unless otherwise specified, lumacaftor, which is used as a starting material is known in the art and can be prepared by the process described in the present specification or may be any methods known in art. The starting lumacaftor may be in any form such as crude obtained directly from the reaction mass, crystalline, amorphous or other forms of lumacaftor, including various solvates and hydrates known in the art as well as the novel crystalline forms described herein the present invention.

In another embodiment, the present invention provides novel crystalline forms of lumacaftor, which are characterized by one or more of analytical techniques such as powder X-Ray diffraction (XRD), differential scanning calorimetry (DSC) and/or thermo gravimetric analysis (TGA).

The X-Ray powder diffraction can be measured using PANalytical X'per³pro X-ray powder Diffractometer equipped with a Cu-anode ([λ]=1.54 Angstrom), X-ray source operated at 45 kV, 40 mA. Two-theta calibration is performed using an NIST SRM 640c Si standard. The sample was analyzed using the following instrument parameters: measuring range=3-45° 2θ; step size=0.01°; and Time per step=50 sec.

All DSC data reported herein were analyzed in hermetically sealed aluminium pan, with an empty hermetically sealed aluminium pan as the reference and were obtained using DSC (DSC Q200, TA instrumentation, Waters) at a scan rate of 10° C. per minute in the range of 50 to 250° C.

All TGA data reported herein were analyzed using TGA Q500 in platinum pan with a temperature rise of about 10° C./min in the range of about room temperature to about 250° C.

In another embodiment, the present invention provides novel crystalline forms of lumacaftor, herein designated as lumacaftor Form-LA1, lumacaftor Form-LA2 and lumacaftor Form-LA3.

In another embodiment, the lumacaftor Form-LA1 of the present invention is an anhydrous crystalline from.

Figure 1:
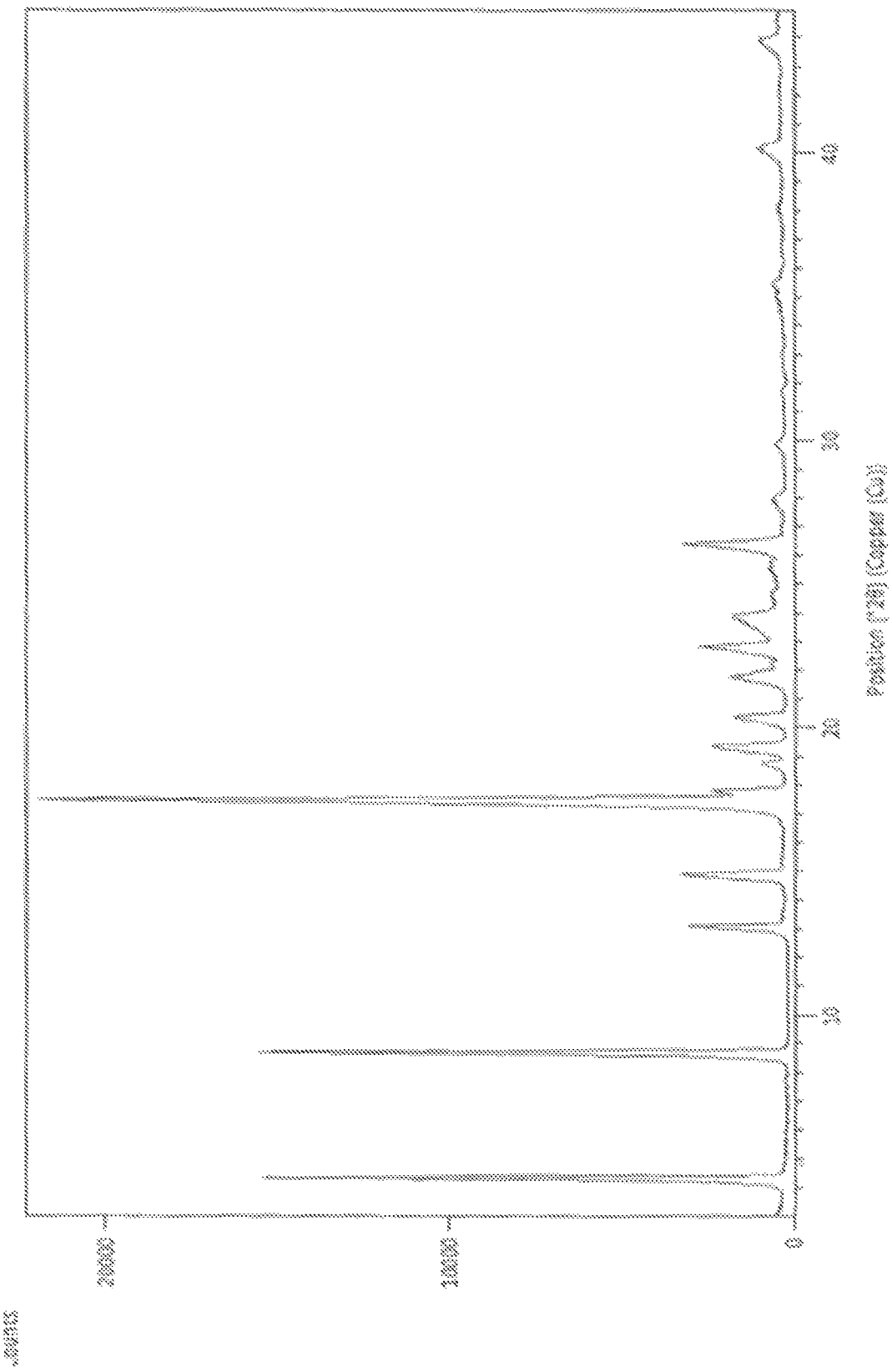
FIG. 1 is the characteristic powder X-ray diffraction (XRD) pattern of lumacaftor Form-LA1.

In another embodiment, the present invention provides lumacaftor Form-LA1 characterized by a powder X-ray diffraction (PXRD) pattern substantially in accordance with FIG. 1.

In another embodiment, the present invention provides lumacaftor Form-LA1 characterized by X-Ray diffraction (XRD) pattern having one or more peaks at about 4.3, 8.7, 12.9, 18.7 and 28.0±0.2° 2θ.

In another embodiment, the present invention provides lumacaftor Form-LA1 further characterized by X-Ray diffraction (XRD) pattern having one or more peaks at about 4.3, 8.7, 12.9, 14.8, 17.5, 17.7, 18.7, 19.3, 20.3, 21.8, 22.2, 22.8, 23.5, 23.6, 25.7, 26.4, 28.0, 29.8, 33.0, 36.9, 38.2, 40.1 and 43.7±0.2° 2θ.

Figure 2:
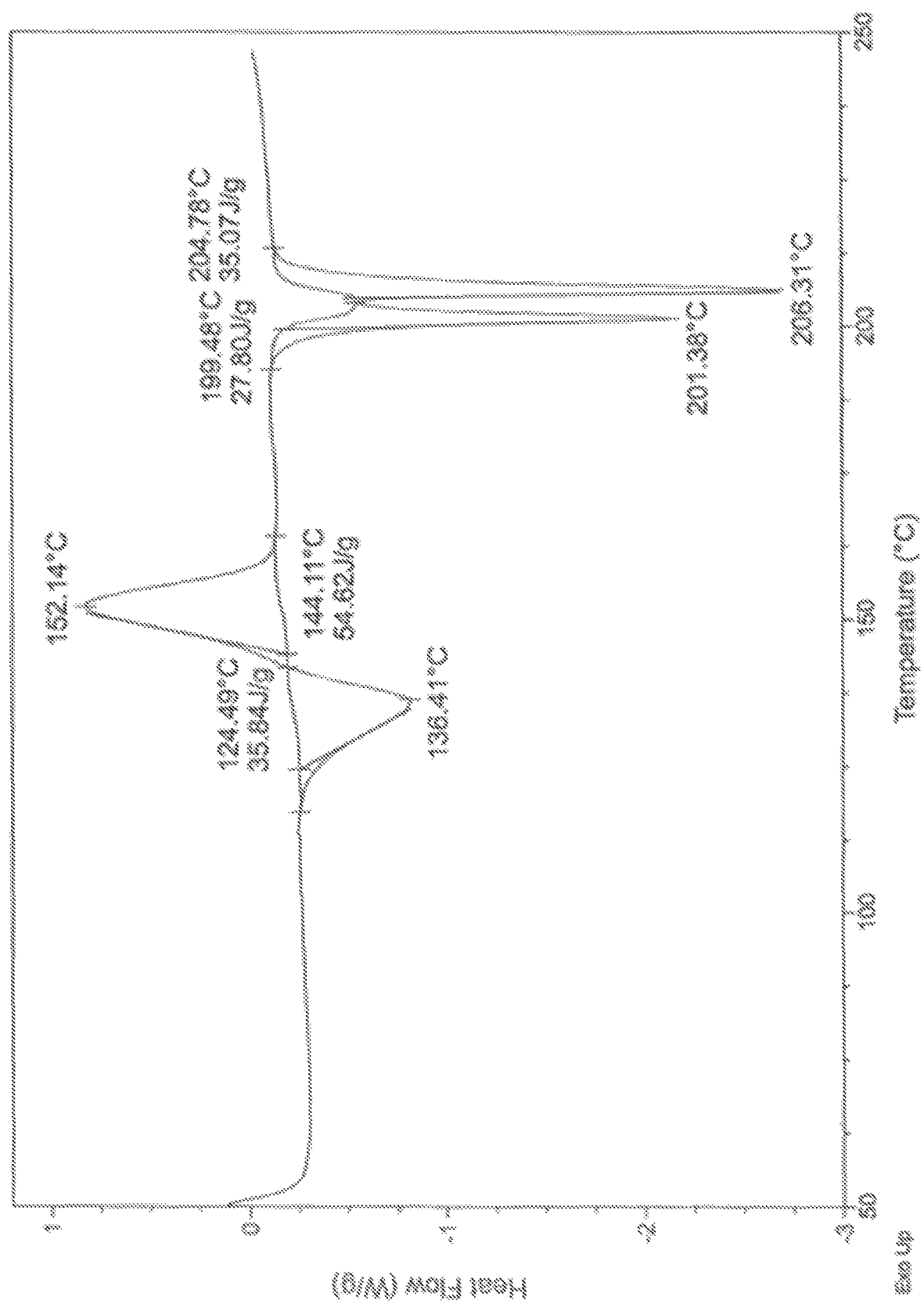
FIG. 2 is the characteristic differential scanning calorimetric (DSC) thermogram of lumacaftor Form-LA1.

In another embodiment, the present invention provides lumacaftor Form-LA1 characterized by a differential scanning calorimetry (DSC) thermogram substantially in accordance with FIG. 2.

Figure 3:
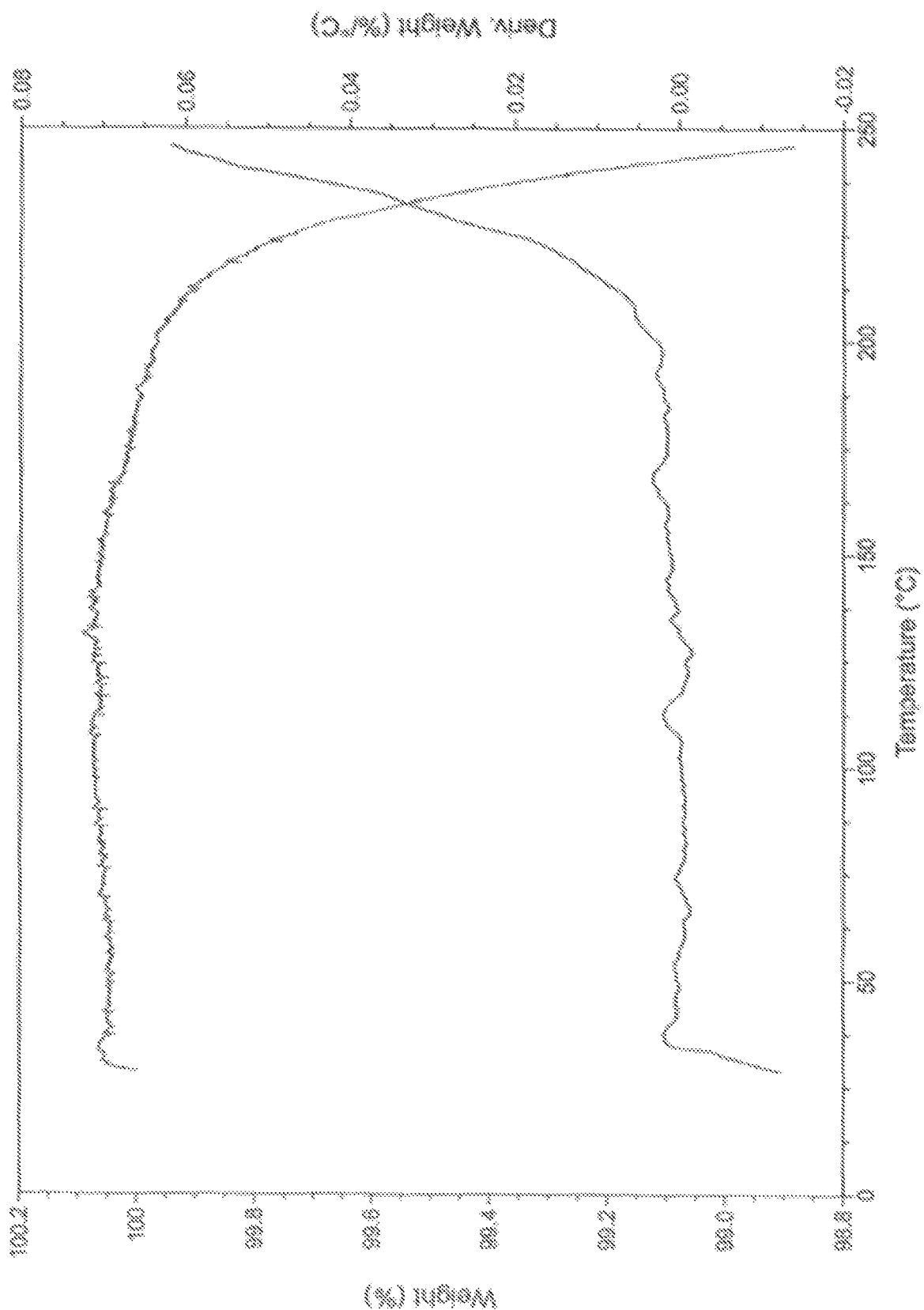
FIG. 3 is the characteristic thermo gravimetric analysis (TGA) thermogram of lumacaftor Form-LA1.

In another embodiment, the present invention provides lumacaftor Form-LA1 characterized by a thermo gravimetric analysis (TGA) curve substantially in accordance with FIG. 3.

In another embodiment, the present invention provides lumacaftor Form-LA1 characterized by X-Ray powder diffraction (XRD) pattern substantially in accordance with FIG. 1, a differential scanning calorimetry (DSC) thermogram substantially in accordance with FIG. 2 and a thermo gravimetric analysis (TGA) curve substantially in accordance with FIG. 3.

In another embodiment, the present invention provides a process for the preparation of lumacaftor Form-LA1, comprising:
 a) dissolving lumacaftor in water and a suitable base at a suitable temperature,
 b) optionally, cooling the solution to less than 25° C., and
 c) isolating the lumacaftor Form-LA1.

In another embodiment, the present invention provides a process for the preparation of lumacaftor Form-LA1, comprising:
 a) dissolving lumacaftor in water and a suitable base at a suitable temperature,
 b) optionally, cooling the solution to less than 25° C., and
 c) isolating the lumacaftor Form-LA1; wherein the suitable base is selected from the group comprising ammonium bases, alkali metal hydroxides, alkali metal alkoxides, alkali metal carbonates, alkali metal bicarbonates or organic bases and mixture thereof.

As used herein, unless otherwise specified, lumacaftor, which is used as a starting material is known in the art and can be prepared by any known methods, for example lumacaftor may be synthesized as disclosed in international PCT publication WO2007/056341 or may be by following the process described in the present specification. The lumacaftor starting material may be any crystalline or other form of lumacaftor, including amorphous, various solvates, hydrates, salts and cocrystals as long as lumacaftor Form-LA1 is produced during the process of the invention or lumacaftor obtaining as existing solution from a previous processing step.

The aforementioned step a) process includes dissolving lumacaftor in water and a suitable base. The dissolution step may optionally further includes first suspending lumacaftor in water and then adding a suitable base or vice-versa and heating the resultant suspension at a suitable temperature of about 35° C. to about reflux; preferably at about 50° C. to about 80° C. to form a clear solution.

The suitable base used herein for dissolving lumacaftor include but is not limited to ammonium bases such as ammonium hydroxide, ammonium carbonate, ammonium bicarbonate and the like; alkali metal hydroxides such as lithium hydroxide, sodium hydroxide, potassium hydroxide and the like; alkali metal alkoxides such as sodium methoxide, sodium ethoxide, sodium tert-butoxide, potassium tert-butoxide and the like; alkali metal carbonates such as sodium carbonate, potassium carbonate, cesium carbonate and the like; alkali metal bicarbonates such as sodium bicarbonate, potassium bicarbonate and the like; organic bases selected from the group comprising of triethylamine, isopropyl ethylamine, diisopropyl amine, diisopropyl ethylamine and the like and mixture thereof; preferably the base used herein for dissolving lumacaftor is ammonium hydroxide, sodium hydroxide, potassium tert-butoxide and mixtures thereof; more preferably ammonium hydroxide.

Step b) of the aforementioned process involves gradually cooling the solution to less than 25° C.; preferably to about 10° C. to about 20° C., for sufficient period of time to precipitate out lumacaftor from the solution, preferably for a period of about 30 min to 5 hours and isolating the lumacaftor Form-LA1 by known methods in the art, for example filtration, decantation. Typically, if stirring is involved, the temperature during stirring can range from about 10° C. to about 25° C. and the resultant product may optionally be further dried at a temperature of about 60° C. to about 75° C.

In a specific embodiment, the present invention provides a process for the preparation of lumacaftor Form-LA1, comprising:
  a) dissolving lumacaftor in water and ammonium hydroxide at a temperature of about 35° C. to reflux temperature,
  b) optionally, cooling the solution to less than 25° C., and
  c) isolating the lumacaftor Form-LA1.

In another specific embodiment, the present invention provides a process for the preparation of lumacaftor Form-LA1, comprising:
  a) suspending lumacaftor in water,
  b) adding ammonium hydroxide to the step a) suspension or vice-versa,
  c) heating the step b) reaction mixture to about 35° C. to reflux temperature,
  d) cooling the step c) reaction mixture to less than 25° C., and
  e) isolating the lumacaftor Form-LA1.

The aforementioned step a) process includes dissolving lumacaftor in water and ammonium hydroxide. The dissolution step may optionally further includes first suspending lumacaftor in water and then adding a ammonium hydroxide or vice-versa and heating the resultant suspension at a temperature of about 35° C. to about reflux temperature; preferably at about 50° C. to about 80° C. to form a clear solution.

Step b) of the aforementioned process involves gradually cooling the solution to about less than 25° C.; preferably to about 10° C. to about 20° C., for sufficient period of time to precipitate out lumacaftor from the solution, preferably for a period of about 30 min to 5 hours and isolating the lumacaftor Form-LA1 by known methods in the art, for example filtration, decantation. Typically, if stirring is involved, the temperature during stirring can range from about 10° C. to about 25° C. and the resultant product may optionally be further dried at a temperature of about 60° C. to about 75° C.

In another embodiment, the present invention provides lumacaftor Form-LA1 prepared by the processes described above, is characterized by X-Ray diffraction (XRD) pattern having one or more peaks at about 4.3, 8.7, 12.9, 14.8, 17.5, 17.7, 18.7, 19.3, 20.3, 21.8, 22.2, 22.8, 23.5, 23.6, 25.7, 26.4, 28.0, 29.8, 33.0, 36.9, 38.2, 40.1 and 43.7±0.2° 2θ.

In another embodiment, the present invention provides lumacaftor Form-LA1 prepared by the processes described above, having a chemical purity of 98% or more as measured by HPLC, preferably 99% or more, more preferably 99.5% or more.

In another embodiment, the present invention provides lumacaftor Form-LA2.

In another embodiment, the lumacaftor Form-LA2 of the present invention is an ammonia solvate.

Figure 4:
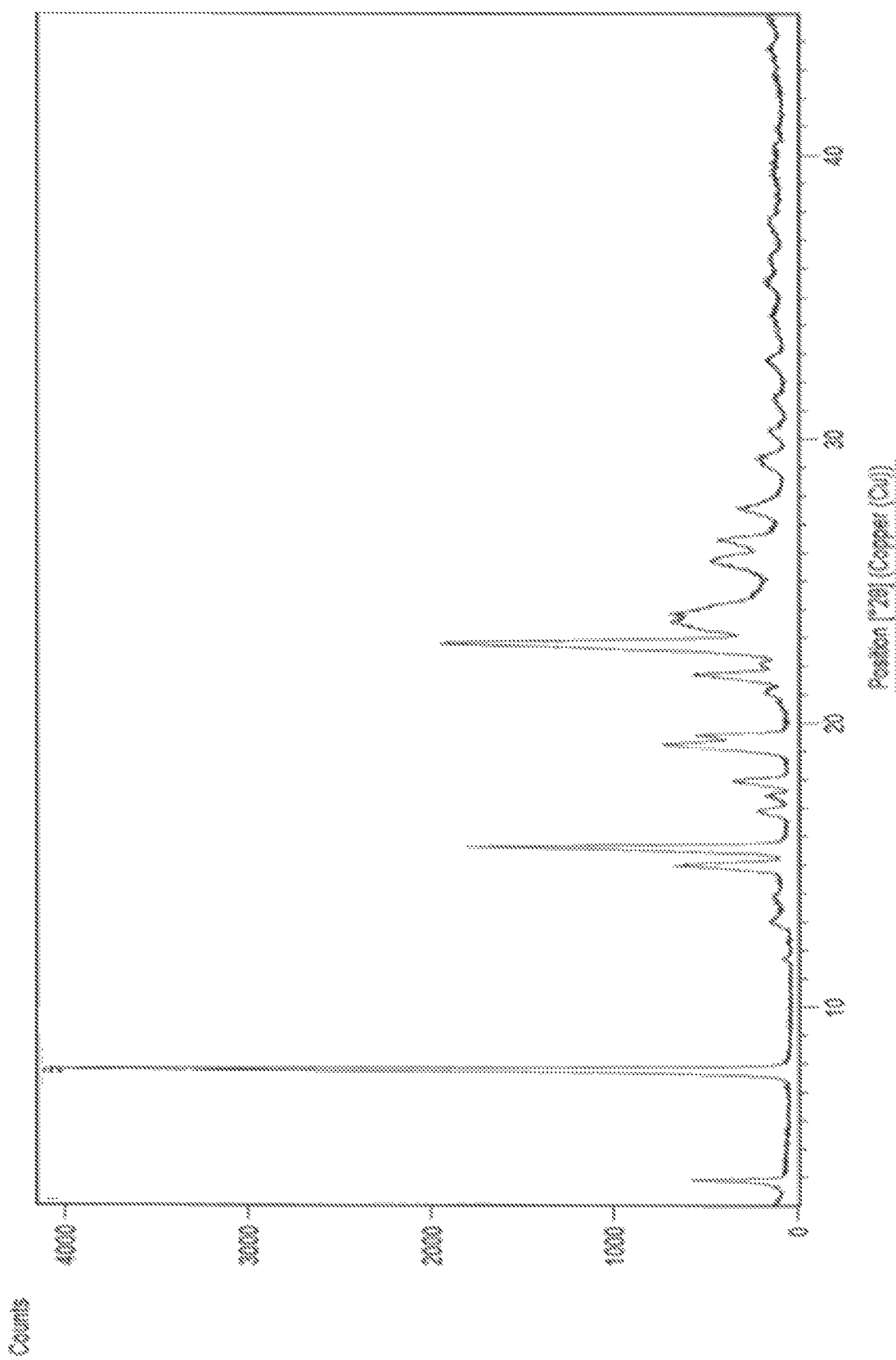
FIG. 4 is the characteristic powder X-ray diffraction (XRD) pattern of lumacaftor Form-LA2.

In another embodiment, the present invention provides lumacaftor Form-LA2 characterized by a powder X-ray diffraction (PXRD) pattern substantially in accordance with FIG. 4.

In another embodiment, the present invention provides lumacaftor Form-LA2 characterized by X-Ray diffraction (XRD) pattern having one or more peaks at about 3.9, 7.7, 11.6, 12.9, 13.8, 14.9, 15.6, 16.8, 17.4, 17.9, 19.1, 19.5, 21.1, 21.7, 22.8, 23.4, 25.7, 26.4, 27.5, 29.2, 30.2, 31.4, 32.7, 33.8, 35.3, 36.2, 37.4, 39.3 and 43.7±0.2° 2θ.

Figure 5:
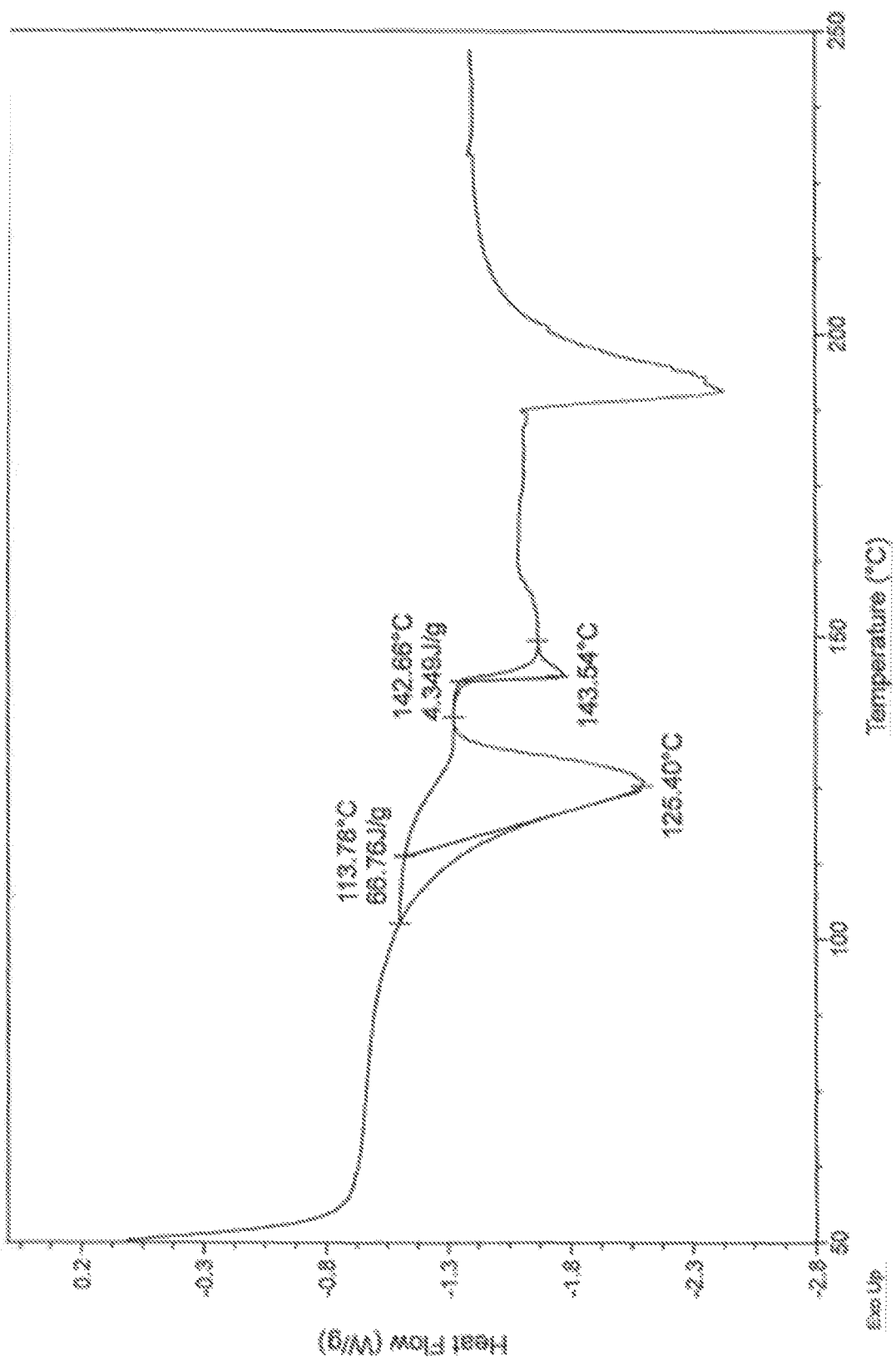
FIG. 5 is the characteristic differential scanning calorimetric (DSC) thermogram of lumacaftor Form-LA2.

In another embodiment, the present invention provides lumacaftor Form-LA2 characterized by a differential scanning calorimetry (DSC) thermogram substantially in accordance with FIG. 5.

Figure 6:
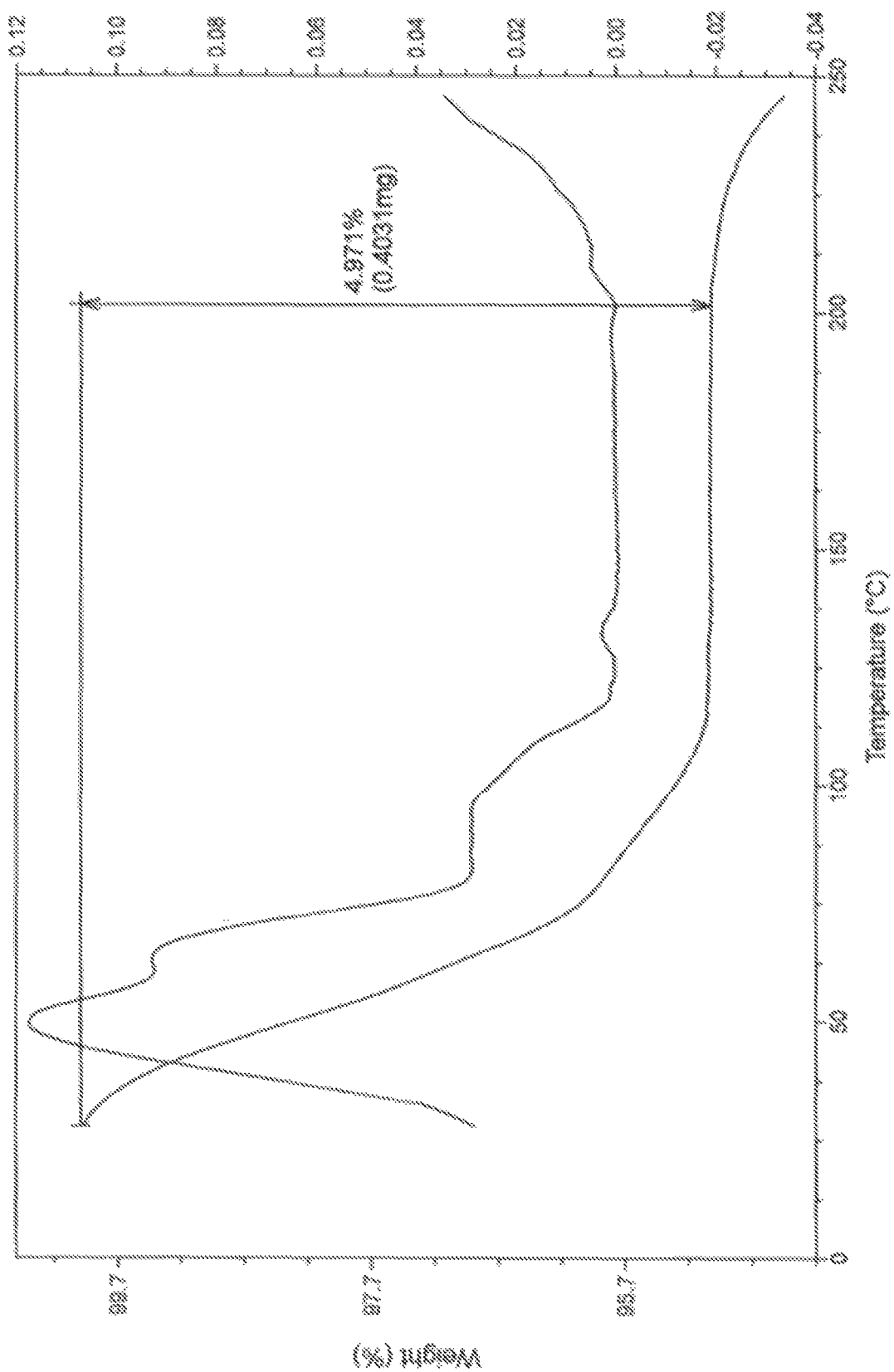
FIG. 6 is the characteristic thermo gravimetric analysis (TGA) thermogram of lumacaftor Form-LA2.

In another embodiment, the present invention provides lumacaftor Form-LA2 characterized by a thermo gravimetric analysis (TGA) curve substantially in accordance with FIG. 6.

In another embodiment, the present invention provides lumacaftor Form-LA2 characterized by X-Ray powder diffraction (XRD) pattern substantially in accordance with FIG. 4, a differential scanning calorimetry (DSC) thermogram substantially in accordance with FIG. 5 and a thermo gravimetric analysis (TGA) curve substantially in accordance with FIG. 6.

In another embodiment, the present invention provides a process for the preparation of lumacaftor Form-LA2, comprising: exposing lumacaftor Form-LA1 under ammonia atmosphere.

The aforementioned process of lumacaftor Form-LA2 includes exposing lumacaftor Form-LA1 under ammonia atmosphere at about 25° C. to about 35° C. for a period of 10 to 30 hours.

In another embodiment, the present invention provides lumacaftor Form-LA3.

In another embodiment, the lumacaftor Form-LA3 of the present invention is an anhydrous crystalline form.

Figure 7:
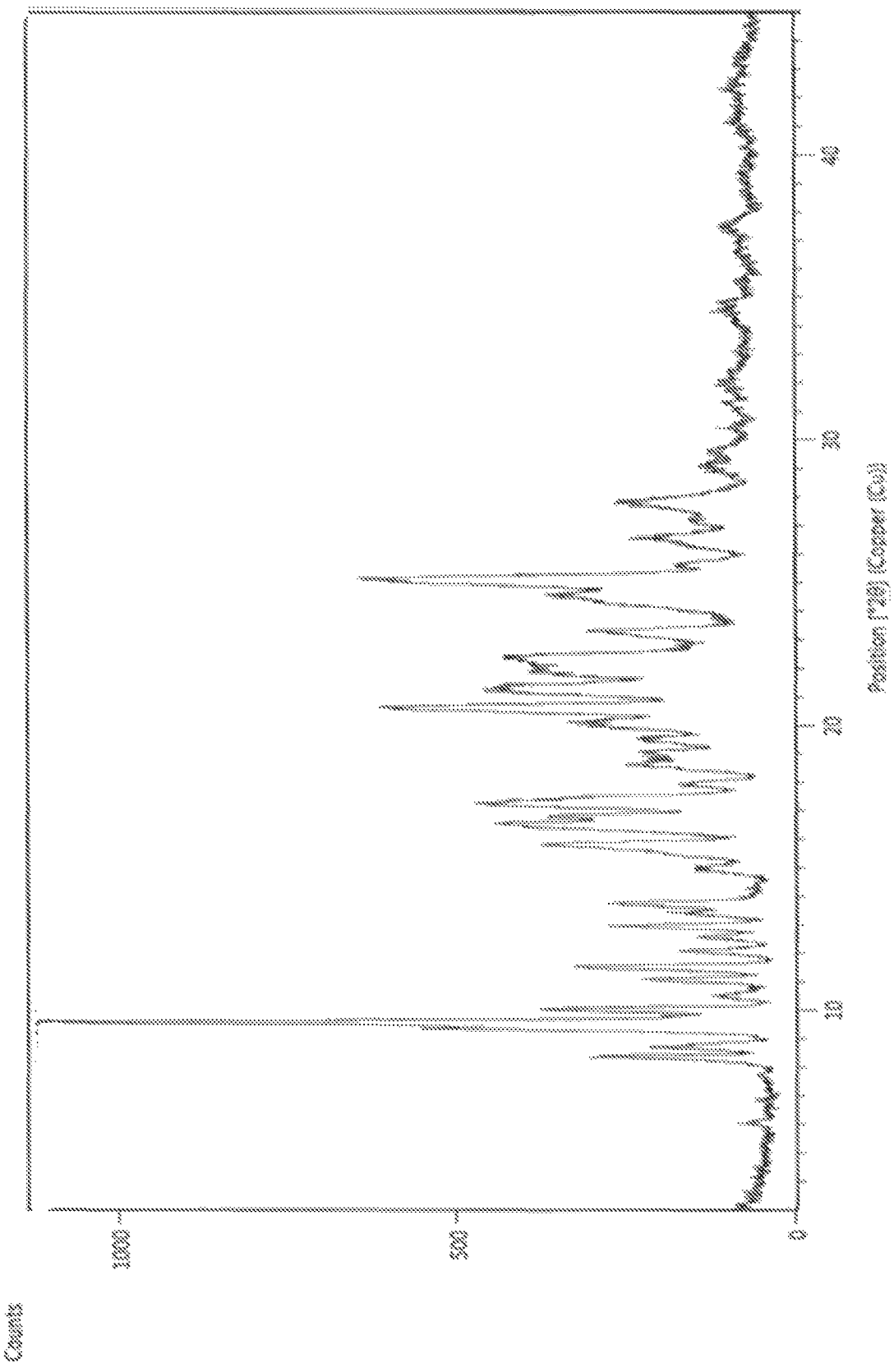
FIG. 7 is the characteristic powder X-ray diffraction (XRD) pattern of lumacaftor Form-LA3.

In another embodiment, the present invention provides lumacaftor Form-LA3 characterized by a powder X-ray diffraction (PXRD) pattern substantially in accordance with FIG. 7.

In another embodiment, the present invention provides lumacaftor Form-LA3 characterized by X-Ray diffraction (XRD) pattern having one or more peaks at about 6.0, 8.3, 8.7, 9.2, 9.6, 10.0, 10.4, 11.0, 11.5, 12.0, 12.5, 12.9, 13.3, 13.7, 14.9, 15.5, 15.8, 16.5, 16.8, 17.3, 17.9, 18.4, 19.0, 19.4, 20.0, 20.6, 21.2, 21.7, 22.4, 23.3, 24.5, 25.1, 25.6, 26.5, 27.9, 28.9 and 37.6±0.2° 2θ.

Figure 8:
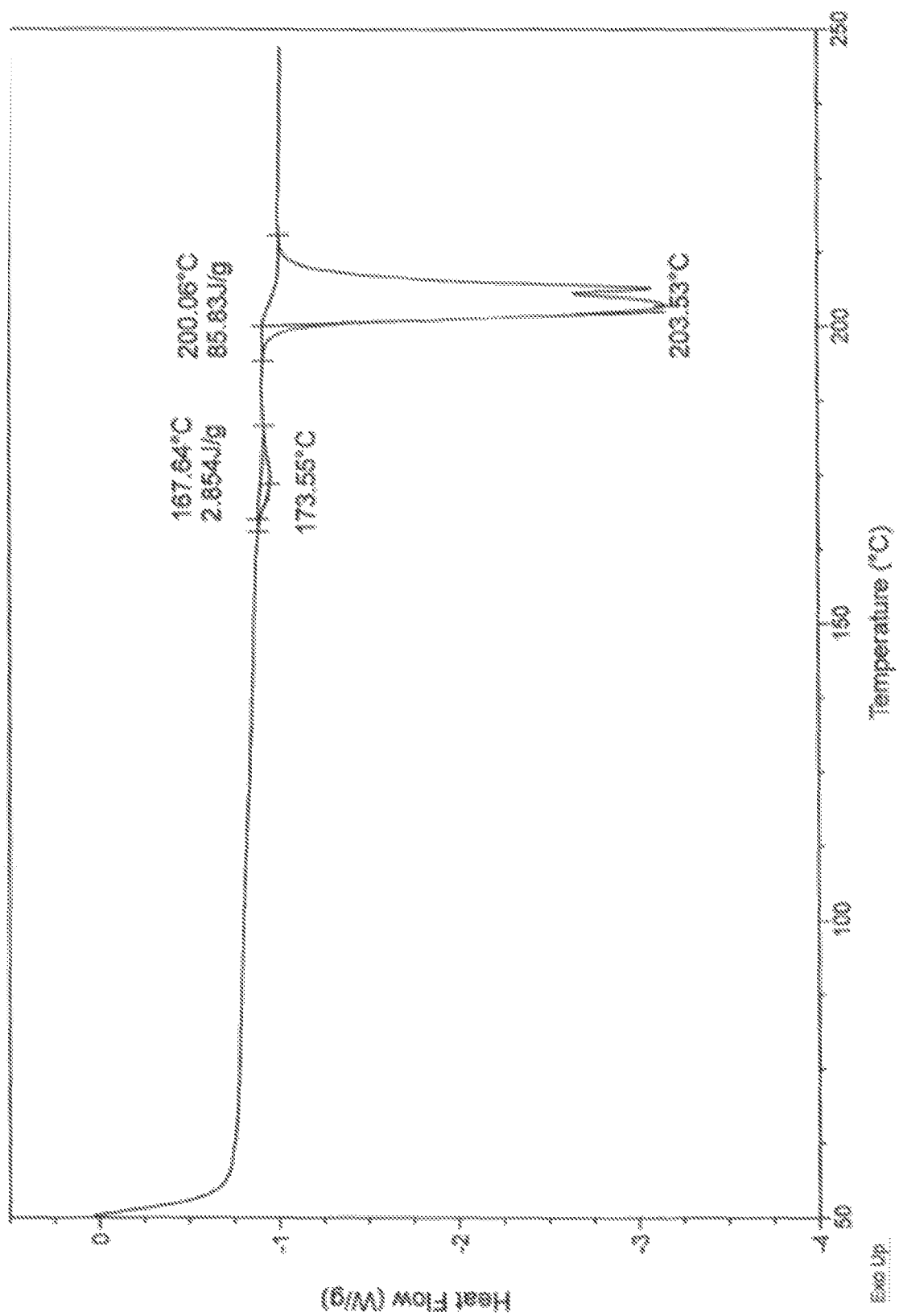
FIG. 8 is the characteristic differential scanning calorimetric (DSC) thermogram of lumacaftor Form-LA3.

In another embodiment, the present invention provides lumacaftor Form-LA3 characterized by a differential scanning calorimetry (DSC) thermogram substantially in accordance with FIG. 8.

Figure 9:
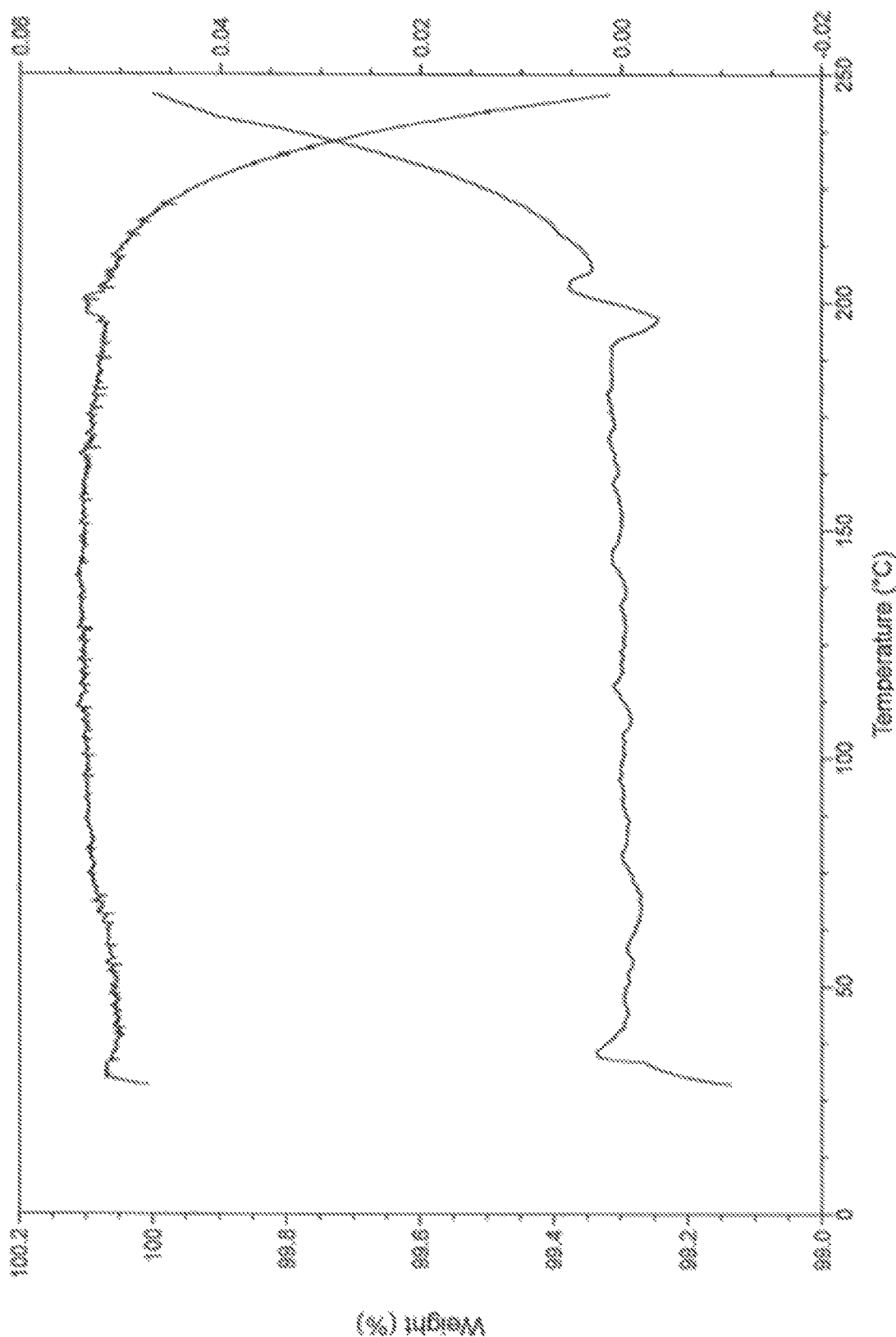
FIG. 9 is the characteristic thermo gravimetric analysis (TGA) thermogram of lumacaftor Form-LA3.

In another embodiment, the present invention provides lumacaftor Form-LA3 characterized by a thermo gravimetric analysis (TGA) curve substantially in accordance with FIG. 9.

In another embodiment, the present invention provides lumacaftor Form-LA3 characterized by X-Ray powder diffraction (XRD) pattern substantially in accordance with FIG. 7, a differential scanning calorimetry (DSC) thermogram substantially in accordance with FIG. 8 and a thermo gravimetric analysis (TGA) curve substantially in accordance with FIG. 9.

In another embodiment, the present invention provides a process for the preparation of lumacaftor Form-LA3, comprising: heating lumacaftor Form-LA1 at about 100° C. to about 140° C.; preferably at about 115° C. to about 125° C. for about 3 to 12 hours.

In another embodiment, the present invention provides a pharmaceutical composition comprising at least one of the novel crystalline forms of lumacaftor described above and at least one or more pharmaceutically acceptable excipients.

In another embodiment, the novel crystalline forms of lumacaftor of the present invention may be used as an intermediate in the preparation of other polymorphic forms of lumacaftor.

In another embodiment, the present invention provides an improved process for the preparation of lumacaftor.

In another embodiment, the present invention provides an improved process for the preparation of lumacaftor.

In another embodiment, the present invention provides an improved process for the preparation of lumacaftor of Formula I, Formula I

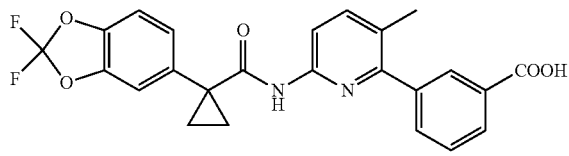

comprising: reacting a compound of Formula II; wherein 'X' represent a suitable leaving group, with a compound of Formula III in presence of a palladium catalyst and base in a suitable solvent to obtain lumacaftor.

Formula II

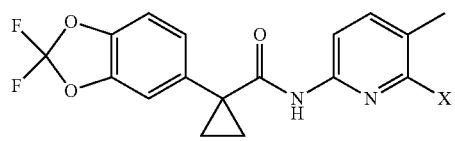

-continued

Formula III

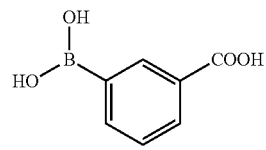

The starting materials, a compound of Formula II and Formula III is known in the art and can be produced by methods known and recognized by the organic chemist of ordinary skill in the art. For example, such a process is described in PCT publication No. WO2007/056341 which is included by reference herein in its entirety.

Generally, microwave support reactions are having many process limitations such as specific equipments, high investment costs, uncontrolled reaction temperatures and pressure and unable to trace reaction progression on multi scale reactions, thereby not suitable for commercial scale manufacturing. For example commercial microwave irradiation reactions rapidly shoot-up power outputs, which increases the reaction internal temperature and pressure, which are uncontrollable at commercial level. Further, due to vigorous heating and microwave rays most often involves formation of dark coloured residues which results nasty workup process and generally required tedious column chromatographic purification, which are not suitable for commercial scale manufacturing process.

The '341 publication discloses a process for preparation of lumacaftor, which involves reaction of compound of Formula III (chloro intermediate) with a compound of Formula II by microwave irradiation at a temperature of about 150° C. The use of special techniques such as reaction by microwave irradiation is not viable for commercial scale operations as this technique involves specialized expensive equipments. The prolonged period of microwave irradiation at 150° C. leads to formation of unwanted process impurities in higher levels. Also the disclosed process involves tedious reverse-phase preparative liquid chromatographic purifications, which contributes significant impact on the final yield and purity, makes the process not viable for large scale manufacturing.

To overcome the difficulties associated with the process described above, the inventors of the present invention have developed an improved process for the preparation of lumacaftor with high product yield and quality and substantially free of impurities, which process replaces cumbersome microwave irradiation with conventional synthesis method, thereby avoiding the formation of impurities.

The reaction of compound of Formula II; wherein 'X' represent a suitable leaving group, with a compound of Formula III is carried out in presence of a palladium catalyst and base in a suitable solvent to obtain lumacaftor.

Unless otherwise specified the term "suitable leaving group" used herein the specification represents a halo group such as chloro, bromo, iodo; OTf (triflate); OTs (tosylate) and the like; preferably the leaving group is Cl or Br.

The palladium catalyst herein used includes, but is not limited to tetrakis (triphenylphosphine) palladium(0), tetrakis(tri(otolyl) phosphine) palladium(0), tris(dibenzylideneacetone) dipalladium(0), [1,1'-bis(diphenylphosphino) ferrocene] dichloropalladium(II), palladium(II) acetate and the like and mixtures thereof; preferably the palladium catalyst is tetrakis (triphenylphosphine) palladium(0).

The base used herein for the reaction of a compound of Formula II; wherein 'X' represent as above, with a compound of Formula III include but is not limited to alkali metal hydroxides such as lithium hydroxide, sodium hydroxide, potassium hydroxide and the like; alkali metal alkoxides such as sodium methoxide, sodium ethoxide, sodium tert-butoxide, potassium tert-butoxide and the like; alkali metal carbonates such as sodium carbonate, potassium carbonate, cesium carbonate and the like; alkali metal bicarbonates such as sodium bicarbonate, potassium bicarbonate and the like; and organic bases such as triethylamine, isopropyl ethylamine, diisopropyl amine, diisopropyl ethylamine, N-methyl morpholine, piperidine, pyridine and the like and their mixtures thereof; preferably the base is potassium carbonate, sodium methoxide and sodium tert-butoxide; more preferably the base is potassium carbonate.

The suitable solvent for reaction of a compound of Formula II; wherein 'X' represent as above, with a compound of Formula III include but is not limit to ethers, amides, sulfoxides, aromatic hydrocarbons, water and mixtures thereof. The ethers include, but are not limited to tetrahydrofuran, 2-methyl tetrahydrofuran, dimethyl ether, diethyl ether, diisopropyl ether, methyl tertiary butyl ether, 1,4-dioxane, 1,2-dimethoxy ethane, and the like; amides include, but not limited to dimethyl formamide, dimethyl acetamide, N-methyl pyrrolidinone and the like; sulfoxides include, but are not limited to dimethyl sulfoxide and the like; aromatic hydrocarbons include, but are not limited to toluene, xylene; water and the like and mixture thereof; preferably the suitable solvent is dimethyl formamide, 1,4-dioxane and toluene; more preferably the suitable solvent is dimethyl formamide.

The reaction of a compound of Formula II; wherein 'X' represent as above, with a compound of Formula III is advantageously carried out at a temperature of about 25° C. to reflux temperature; preferably at about 85° C. to about 105° C.

After completion of the reaction, the resultant reaction mass may be cooled to about 25° C. to about 35° C. Then water may be charged to the reaction mass and washed the reaction mass with a suitable water immiscible organic solvent such as toluene, ethyl acetate, methylene chloride and the like; preferably with toluene. Then the product containing aqueous layer again charged with a suitable water immiscible organic solvent such as toluene, ethyl acetate, methylene chloride and the like; preferably with methylene chloride and then pH adjusted to 4.5±0.5 with suitable acid such as hydrochloric acid, acetic acid and the like. Then the product containing water immiscible organic solvent may be separated and evaporated under vacuum to obtain a residue. Then the residue may be dissolved in organic solvent such as methylene chloride at temperature of about 25° C. to about 45° C. and then cooling the solution to about less than 20° C. to precipitate solid lumacaftor. The precipitated lumacaftor may be separated by methods known in the art, for example filtration.

In another embodiment, the above obtained lumacaftor may be used as an intermediate in the preparation of novel polymorphic forms of the present invention.

In another embodiment, the above obtained lumacaftor may be used as an intermediate in the preparation of lumacaftor Form-LA1, Form-LA2 or Form-LA3 of the present invention.

In another embodiment, the present invention provides a process for the preparation of lumacaftor Form-LA1, comprising:
a) reacting a compound of Formula II; wherein 'X' represent a suitable leaving group, with a compound of Formula III in presence of a palladium catalyst and base in a suitable solvent to obtain lumacaftor,
b) dissolving the lumacaftor of step a) in water and a suitable base at a suitable temperature,
c) optionally, cooling the solution to less than 25° C., and
d) isolating the lumacaftor Form-LA1.

Preparation of Lumacaftor of step a) and its conversion to Lumacaftor form LA1 is carried out by the processes described as above of the present invention.

In another embodiment, the present invention provides lumacaftor prepared by the processes described above, having a chemical purity of 98% or more as measured by HPLC, preferably 99% or more, more preferably 99.5% or more.

In another embodiment, the present invention provides lumacaftor Form-LA1, Form-LA2 or Form-LA3 prepared by the processes described above, having a chemical purity of 98% or more as measured by HPLC, preferably 99% or more, more preferably 99.5% or more.

In another embodiment, the present invention provides the use of novel crystalline forms of lumacaftor Form-LA1, Form-LA2 or Form-LA3 as an intermediate to prepare other polymorphic forms of lumacaftor.

In another embodiment, the present invention provides a process for the preparation of lumacaftor Form I, comprising:
a) suspending lumacaftor Form-LA1 in a suitable solvent; and
b) isolating the lumacaftor Form I.

The Lumacaftor Form I is a known compound and is disclosed in the literature, for example, disclosed in the U.S. Pat. No. 8,507,534.

The starting material of Lumacaftor Form-LA1 can be prepared according to the process of present invention described herein above.

The step a) of providing a suspension of lumacaftor Form-LA1 in a suitable solvent; preferably in water, may include heating the reaction mass to a temperature of about 50° C. to about reflux temperature, preferably to a temperature of about 65° C. to about 75° C.

The step b) of isolation of lumacaftor Form-I, may include cooling the reaction mass to a temperature of about 25-35° C. such that the lumacaftor Form-I can be precipitated from the reaction mass and can be isolated by conventional techniques such as filtration. The resultant wet product may optionally be further dried. Drying can be suitably carried out in a tray dryer, vacuum oven, air oven, fluidized bed drier, spin flash dryer, flash dryer and the like.

Suitable pharmaceutical compositions are solid dosage forms, such as tablets with immediate release or sustained release of the active principle, effervescent tablets or dispersion tablets and capsules. Optionally, the pharmaceutical compositions of the invention may be combination products comprising one or more additional pharmaceutically active components in addition to lumacaftor.

EXAMPLES

The following non limiting examples illustrate specific embodiments of the present invention. They are not intended to be limiting the scope of the present invention in any way.

Example 1

Preparation of Lumacaftor
Dimethyl formamide (500 mL), compound of Formula II (100 g; X=Br) and potassium carbonate solution (162 g dissolved in 620 mL water) were charged in a reaction flask at 25-35° C. To the reaction mass compound of Formula III (48.4 g) and Pd(PPh$_3$)$_4$ (4.21 g) were charged at 25-35° C., heated to 85-95° C. and stirred for 1 hr at same temperature. After completion of the reaction, filtered the reaction mass and diluted the filterate with toluene (300 mL) and water (700 mL) and stirred for 10 min at 25-35° C. Then the product containing aqueous layer was separated and charged methylene chloride (300 mL) to the aqueous layer. Reaction mass pH was adjusted to 4-5 with hydrochloric acid solution at 25-35° C. and stirred for 1 hr at same temperature. Then the product containing organic layer was separated and concentrated at below 80° C. to obtain a residue. The obtained residue was dissolved in methylene chloride (300 mL) at 25-35° C. and stirred for 60 min at same temperature. Reaction mass was allowed to cool to 15-25° C. The solid was isolated by filtration and washed with methylene chloride (100 mL) and dryed at 50-55° C. to obtain lumacaftor. Yield: 95 gm.

Example 2: Preparation of Lumacaftor

Dimethyl formamide (700 mL), compound of Formula II (100 g; X=Cl) and Formula III (54.3 g) were charged in a reaction flask at 25-35° C. To the reaction mass added potassium carbonate solution (181 g dissolved in 620 mL water) and Pd(PPh$_3$)$_4$ (4.7 g) were charged at 25-35° C., heated to 100-105° C. and stirred for 1-3 hrs at same temperature. After completion of the reaction, reaction mass allowed to cool to 25-35° C. and charged water (700 ml) at same temperature. Reaction mass was washed with toluene (2×300 mL). Then the product containing aqueous layer was separated and charged methylene chloride (500 mL) to the aqueous layer. Reaction mass pH was adjusted to 4-5 with hydrochloric acid solution at 25-35° C. and stirred for 1 hr at same temperature. Then the product containing organic layer was separated and concentrated at atmospheric pressure up to 3-4 vol remains in the flask and strip off with toluene (2×100 mL) and methylene chloride (100 mL) at below 75° C. to obtain a residue. The obtained residue was dissolved in methylene chloride (100 mL) at 25-35° C. and stirred for 60 min at same temperature. Reaction mass was allowed to cool to 15-25° C. The solid was isolated by filtration and washed with methylene chloride (100 mL) and dryed at 50-55° C. to obtain lumacaftor. Yield: 110 gm.

Example 3

Preparation of Lumacaftor Form-LA1

Lumacaftor (100 g; from Ex-2), water (400 mL) and ammonium hydroxide (35 mL) were added in to a round bottom flask at 25-35° C. Reaction mass was heated to 65-75° C. to obtain clear solution. Reaction mass was allowed to cool to 35-45° C. and stirred for 30-60 min at same temperature. Reaction mass was further allowed to cool to 15-25° C. and stirred for 1-2 hrs at same temperature. The precipitated solid was isolated by filtration and washed with water (2×100 mL) and dryed at 65-75° C. to obtain lumacaftor Form-LA1. Yield: 95 gm; Purity by HPLC—99.98%; PXRD—FIG. 1; DSC—FIG. 2 and TGA—FIG. 3.

Example 4

Preparation of Lumacaftor Form-LA2
Lumacaftor Form-LA1 (100 gms) was kept in a desiccator in a medium of ammonia solution (35 mL) for 24 hrs to obtain lumacaftor Form-LA2. Yield: 101 gm; Purity by HPLC—100%; PXRD—FIG. 4; DSC—FIG. 5 and TGA—FIG. 6.

Example 5

Preparation of Lumacaftor Form-LA3
Lumacaftor Form-LA1 (100 gms) was dryed in vacuum oven at 115-125° C. for 6 hrs to obtain lumacaftor Form-LA3. Yield: 99 gm; Purity by HPLC—99.93%; PXRD—FIG. 7; DSC—FIG. 8 and TGA—FIG. 9.

Example 6

Preparation of Lumacaftor Form-I from Lumacaftor Form-LA1:

Lumacaftor Form-LA1 (1 g) and water were added into a round bottom flask at 25-35° C. The temperature of the reaction mass was raised to 65-75° C. and maintained for 3-5 hrs. The solution was gradually cool to 20-30° C., filtered and dried at 60° C. to obtain Lumacaftor Form-I. Yield: 0.9 g; HPLC purity 99.96%.

It will be understood that various modifications may be made to the embodiments disclosed herein. Therefore the above description should not be constructed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

The invention claimed is:

1. Lumacaftor Form-LA1 characterized by X-Ray diffraction (XRD) pattern having one or more peaks at about 4.3, 8.7, 12.9, 14.8, 17.5, 17.7, 18.7, 19.3, 20.3, 21.8, 22.2, 22.8, 23.5, 23.6, 25.7, 26.4, 28.0, 29.8, 33.0, 36.9, 38.2, 40.1 and 43.7±0.2° 2θ.

2. Lumacaftor Form-LA1 of claim 1, further characterized by a powder X-ray diffraction (PXRD) pattern in accordance with FIG. 1.

3. Lumacaftor Form-LA1 of claim 1, further characterized by differential scanning calorimetry (DSC) thermogram in accordance with FIG. 2.

4. Lumacaftor Form-LA1 of claim 1, further characterized by thermo gravimetric analysis (TGA) curve in accordance with FIG. 3.

5. Lumacaftor Form-LA1 of claim 1, further characterized by differential scanning calorimetry (DSC) thermogram substantially in accordance with FIG. 2 and a thermo gravimetric analysis (TGA) curve in accordance with FIG. 3.

6. A process for the preparation of lumacaftor Form-LA1, comprising:
   a) dissolving lumacaftor in water and a base at a suitable temperature,
   b) optionally, cooling the solution to less than 25° C., and
   c) isolating the lumacaftor Form-LA1, wherein the Lumacaftor Form-LA1 is characterized by an X-Ray diffraction (XRD) pattern having one or more peaks at about 4.3, 8.7, 12.9, 14.8, 17.5, 17.7, 18.7, 19.3, 20.3, 21.8, 22.2, 22.8, 23.5, 23.6, 25.7, 26.4, 28.0, 29.8, 33.0, 36.9, 38.2, 40.1 and 43.7±0.2° 2θ.

7. The process of claim 6, wherein the base is selected from one or more of the group consisting of ammonium bases, alkali metal hydroxides, alkali metal alkoxides, alkali metal bicarbonates, organic bases, and mixture thereof.

8. The process of claim 7, wherein the base is selected from one or more of the group consisting of ammonium hydroxide, ammonium carbonate, ammonium bicarbonate, lithium hydroxide, sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, isopropyl ethylamine, diisopropyl amine, diisopropyl ethylamine, and mixture thereof.

9. The process of claim 8, wherein the base is ammonium hydroxide.

10. The process of claim 6, wherein the step a) is carried out at a temperature of about 50° C. to 80° C.

11. An improved process for the preparation of lumacaftor of Formula I,

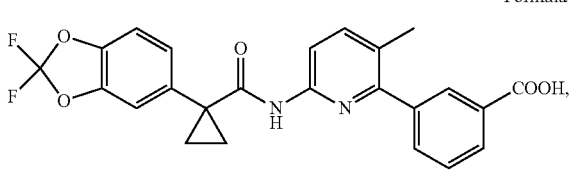

Formula I comprising:
reacting a compound of Formula II with a compound of Formula III in the presence of a palladium catalyst and a base in a solvent to obtain the lumacaftor, wherein 'X' represents a leaving group

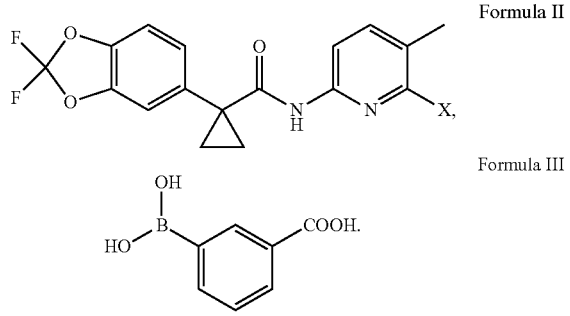

Formula II

Formula III

12. The process of claim 11, wherein the leaving group is selected from one of the group consisting of chloro, bromo, iodo, triflate, and tosylate.

13. The process of claim 12, wherein the leaving group is selected from the group consisting of chloro and bromo.

14. The process of claim 11, wherein the palladium catalyst is selected from one of the group consisting of tetrakis (triphenylphosphine) palladium(0), tetrakis(tri (otolyl) phosphine)palladium(0), tris(dibenzylideneacetone) dipalladium(0), [1,1'-bis(diphenyl phosphino) ferrocene] dichloropalladium (II), and palladium(II) acetate.

15. The process of claim 11, wherein the base is selected from the group consisting of lithium hydroxide, sodium hydroxide, potassium hydroxide, sodium methoxide, sodium ethoxide, sodium tert-butoxide, potassium tert-butoxide, sodium carbonate, potassium carbonate, cesium carbonate, sodium bicarbonate, potassium bicarbonate, triethylamine, isopropyl ethylamine, diisopropyl amine, diisopropyl ethylamine, N-methyl morpholine, piperidine, and pyridine.

16. The process of claim 11, wherein the solvent is selected from one or more of the group consisting of tetrahydrofuran, 2-methyl tetrahydrofuran, dimethyl ether, diethyl ether, diisopropyl ether, methyl tertiary butyl ether, 1,4-dioxane, 1,2-dimethoxy ethane, dimethyl formamide, dimethyl acetamide, N-methyl pyrrolidinone, dimethyl sulfoxide, toluene, xylene, water, and mixture thereof.

17. The process of claim 11, wherein the palladium catalyst is tetrakis (triphenylphosphine) palladium(0); the base is potassium carbonate; and the solvent is dimethyl formamide.

18. The process of claim 11, wherein the reaction is carried out at a temperature of about 85° C. to 105° C.

19. A process for the preparation of lumacaftor Form I, comprising:
a) suspending lumacaftor Form-LA1 in a solvent, wherein the Lumacaftor Form-LA1 is characterized by an X-Ray diffraction (XRD) pattern having one or more peaks at about 4.3, 8.7, 12.9, 14.8, 17.5, 17.7, 18.7, 19.3, 20.3, 21.8, 22.2, 22.8, 23.5, 23.6, 25.7, 26.4, 28.0, 29.8, 33.0, 36.9, 38.2, 40.1 and 43.7±0.2° 2θ; and
b) isolating the lumacaftor Form I.

20. The process of claim 19, wherein the solvent is water.

21. The process of claim 19, wherein the step a) is carried out at a temperature of about 65° C. to 75° C.

22. A pharmaceutical composition comprising:
lumacaftor according to claim 1; and
at least one pharmaceutically acceptable excipient.

* * * * *